US00PP32660P3

(12) United States Plant Patent
Winslow

(10) Patent No.: US PP32,660 P3
(45) Date of Patent: Dec. 15, 2020

(54) ***SUTERA* PLANT NAMED 'WINSUSNOGB'**

(50) Latin Name: *Sutera cordata*
Varietal Denomination: WINSUSNOGB

(71) Applicant: Benjamin Kent Winslow, Austin, TX (US)

(72) Inventor: Benjamin Kent Winslow, Austin, TX (US)

( * ) Notice: Subject to any disclaimer, the term of this patent is extended or adjusted under 35 U.S.C. 154(b) by 0 days.

(21) Appl. No.: 16/873,416

(22) Filed: Apr. 9, 2020

(65) Prior Publication Data

US 2020/0329621 P1 Oct. 15, 2020

(30) Foreign Application Priority Data

Apr. 10, 2019 (CA) ..... PBR 19-9754

(51) Int. Cl.
*A01H 5/02* (2018.01)
*A01H 6/00* (2018.01)

(52) U.S. Cl.
USPC ..... Plt./485
CPC ..... *A01H 6/00* (2018.05); *A01H 5/02* (2013.01)

(58) Field of Classification Search
USPC ..... Plt./485
See application file for complete search history.

*Primary Examiner* — Susan McCormick Ewoldt
(74) *Attorney, Agent, or Firm* — C. A. Whealy

(57) ABSTRACT

A new and distinct cultivar of *Sutera* plant named 'WINSUSNOGB' characterized by its low mounding to outwardly spreading and trailing plant habit; moderately vigorous growth habit; freely branching habit; dense and bushy plant form; early and freely flowering habit; large white-colored flowers; long flowering season; and good garden performance.

1 Drawing Sheet

Botanical designation: *Sutera cordata.*
Cultivar denomination: 'WINSUSNOGB'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on Apr. 10, 2019, application number 19-9754. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Sutera* plant, botanically known as *Sutera cordata* and hereinafter referred to by the name 'WINSUSNOGB'.

The new *Sutera* plant is a product of a planned breeding program conducted by the Inventor in Alajuela, Costa Rica. The objective of the breeding program is to create new freely-branching and trailing *Sutera* plants with numerous large blue-colored flowers and high temperature tolerance.

The new *Sutera* plant originated from a cross-pollination conducted by the Inventor in November, 2016 in Alajuela, Costa Rica of two unnamed proprietary selections of *Sutera cordata*, not patented. The new *Sutera* plant was discovered and selected by the Inventor as a flowering plant from within the progeny of the stated cross-pollination in a controlled greenhouse environment in Alajuela, Costa Rica on Sep. 8, 2017.

Asexual reproduction of the new *Sutera* plant by terminal vegetative cuttings in a controlled greenhouse environment in Zeeland, Mich. since Oct. 6, 2017 has shown that the unique features of this new *Sutera* plant are stable and reproduced true to type in successive generations.

SUMMARY OF THE INVENTION

Plants of the new *Sutera* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WINSUSNOGB'. These characteristics in combination distinguish 'WINSUSNOGB' as a new and distinct *Sutera* plant:

1. Low mounding to outwardly spreading and trailing plant habit.
2. Moderately vigorous growth habit.
3. Freely branching habit; dense and bushy plant form.
4. Early and freely flowering habit.
5. Large white-colored flowers.
6. Long flowering season.
7. Good garden performance.

Plants of the new *Sutera* can be compared to plants of the parent selections. Plants of the new *Sutera* differ primarily from plants of the parent selections in the following characteristics:

1. Plants of the new *Sutera* are more vigorous and stronger than plants of the parent selections.
2. Plants of the new *Sutera* have larger flowers than plants of the parent selection.

Plants of the new *Sutera* can be compared to plants of the *Sutera cordata* 'Danova780', disclosed in U.S. Plant Pat. No. 26,789. In side-by-side comparisons, plants of the new *Sutera* differ primarily from plants of 'Danova780' in the following characteristics:

1. Plants of the new *Sutera* are larger than plants of 'Danova780'.
2. Plants of the new *Sutera* have larger flowers than plants of 'Danova780'.
3. Plants of the new *Sutera* are more freely flowering and flower more continuously during the summer than plants of 'Danova780'.

Plants of the new *Sutera* can be compared to plants of the *Sutera cordata* 'Danova906', disclosed in U.S. Plant Pat. No. 17,886. In side-by-side comparisons, plants of the new *Sutera* differ primarily from plants of 'Danova906' in the following characteristics:

1. Plants of the new *Sutera* are not as trailing as plants of 'Danova906'.
2. Plants of the new *Sutera* have larger flowers than plants of 'Danova906'.
3. Plants of the new *Sutera* are more freely flowering and flower more continuously during the summer than plants of 'Danova906'.

BRIEF DESCRIPTION OF THE PHOTOGRAPHS

The accompanying colored photographs illustrate the overall appearance of the new *Sutera* plant showing the colors as true as it is reasonably possible to obtain in colored reproductions of this type. Colors in the photographs may differ slightly from the color values cited in the detailed botanical description which accurately describe the colors of the new *Sutera* plant.

At the top of the photographic sheet (FIG. 1) is a side perspective view of a typical flowering plant of 'WINSUSNOGB' grown in a container and at the bottom of the photographic sheet is a close-up view of a typical flowering plant of 'WINSUSNOGB'.

DETAILED BOTANICAL DESCRIPTION

The aforementioned photographs and following observations and measurements describe plants grown during the spring in 15-cm containers in a polyethylene-covered greenhouse in St. Thomas, Ontario, Canada and under cultural practices typical of commercial *Sutera* production. During the production of the plants, day temperatures averaged 27° C. and night temperatures averaged 15° C. Plants were pinched three weeks after propagating rooted cuttings and were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Sutera cordata* 'WINSUSNOGB'.

Parentage:

*Female, or seed, parent*.—Unnamed proprietary selection of *Sutera cordata*, not patented.

*Male or pollen parent*.—Unnamed proprietary selection of *Sutera cordata*, not patented.

Propagation:

*Type*.—By terminal vegetative cuttings.

*Time to initiate roots, summer and winter*.—About seven to ten days at soil temperatures ranging from about 21° C. to 22° C.

*Time to produce a rooted young plant, summer*.—About three to four weeks at soil temperatures ranging from about 21° C. to 22° C.

*Time to produce a rooted young plant, winter*.—About four to five weeks at soil temperatures ranging from about 21° C. to 22° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Low mounding to outwardly spreading and trailing plant habit; moderately vigorous growth habit; moderate growth rate.

*Plant height*.—About 11.8 cm.

*Plant diameter* (*area of spread*).—About 46.9 cm.

Lateral branch description:

*Branching habit*.—Freely branching habit; when pinched, about four primary lateral branches each with up to 16 secondary lateral branches develop per plant; dense and bushy plant form.

*Length, primary laterals*.—About 25.5 cm.

*Diameter, primary laterals*.—About 2.7 mm.

*Internode length*.—About 2.2 cm.

*Strength*.—Moderately strong.

*Aspect*.—Horizontally spreading to trailing.

*Texture and luster*.—Moderately to densely pubescent; matte.

*Color, developing*.—Close to 144B.

*Color, developed*.—Close to 148A; at the internodes, close to 147A.

Leaf description:

*Arrangement*.—Before flowering, alternate; after flowering, opposite, simple.

*Length*.—About 2.5 cm.

*Width*.—About 2.3 cm.

*Shape*.—Broadly elliptic.

*Apex*.—Acute.

*Base*.—Cuneate.

*Margin*.—Dentate, not lobed.

*Texture and luster, upper and lower surfaces*.—Sparsely pubescent; matte.

*Venation pattern*.—Pinnate, reticulate.

*Color*.—Developing leaves, upper surface: Close to 138A. Developing leaves, lower surface: Close to 138B. Fully expanded leaves, upper surface: Close to 147A; venation, close to 144B. Fully expanded leaves, lower surface: Close to 147B; venation, close to 144B.

*Petioles*.—Length: About 6 mm. Diameter: About 2 mm. Strength: Moderately strong. Texture and luster, upper and lower surfaces: Moderately pubescent; matte. Color, upper and lower surfaces: Close to 144A.

Flower description:

*Flower arrangement*.—Large single salverform flowers; freely flowering habit with potentially about 720 flower buds and open flowers per plant at one time; flowers face mostly upright then turning outwardly.

*Fragrance*.—None detected.

*Flowering habit*.—Early flowering habit, plants begin flowering about five weeks after planting; long flowering season, plants flower continuously from the spring until the autumn in Southern Ontario.

*Flower longevity*.—Flowers last about five days on the plant; flowers not persistent.

*Flower diameter*.—About 2.7 cm.

*Flower length* (*height*).—About 1.3 cm.

*Throat diameter*.—About 7 mm.

*Tube length*.—About 1 cm.

*Tube diameter, base*.—About 1.5 mm.

*Flower buds*.—Length: About 11 mm. Diameter: About 4.8 mm. Shape: Obovate. Texture and luster: Densely pubescent; matte. Color: Close to N155A; at the base, close to 163C.

*Petals*.—Quantity and arrangement: Five per flower in a single whorl; fused at the base. Lobe length: About 9.4 mm. Lobe width: About 11 mm. Lobe shape: Roughly orbicular. Lobe apex: Obtuse, rounded. Lobe margin: Entire, slightly to moderately undulate. Texture and luster, petal lobes, upper surface: Smooth, glabrous; matte. Texture and luster, petal lobes, lower surface: Slightly to moderately pubescent; matte. Texture and luster, throat: Moderately pubescent, matte. Texture and luster, tube: Densely pubescent, matte. Color. Petal lobes, when opening, upper and lower surfaces: Close to NN155B. Petal lobes, fully opened, upper and lower surfaces. Close to NN155B; venation, close to NN155B; color does not change with development. Throat: Close to 23A. Tube: Close to 22B and towards the base, close to 157D.

*Sepals*.—Quantity and arrangement: Five per flower in a single whorl; fused at the base; calyx, star-shaped. Length: About 5.8 mm. Width: Less than 1 mm. Shape: Lanceolate to linear. Apex: Acute. Margin: Entire. Texture and luster, upper surface: Slightly pubescent; matte. Texture and luster, lower surface: Slightly to moderately pubescent; matte. Color. When opening, upper and lower surfaces: Close to 144A. Fully opened, upper and lower surfaces: Close to 146A.

*Peduncles*.—Length: About 13.2 mm. Diameter: Less than 1 mm. Angle: About 30° from vertical. Strength: Moderately strong. Texture and luster: Moderately to densely pubescent; matte. Color: Close to 137B.

*Reproductive organs*.—Androecium. Quantity of stamens per flower: About four. Filament length: About 1 cm. Filament color: Close to 157D. Anther size: About 1.5 mm by 1 mm. Anther shape: Oval. Anther color: Close to 13A. Amount of pollen: Moderate. Pollen color: Close to 14A. Gynoecium. Quantity of pistils per flower: One. Pistil length: About 1.3 cm. Style length: About 1 cm. Style color: Close to 145B. Stigma size: About 1 mm by 2 mm. Stigma shape: Lanceolate. Stigma color: Close to 145B. Ovary color: Close to 144A.

*Seeds and fruits*.—To date, seed and fruit production have not been observed on plants of the new *Sutera*.

Garden performance: Plants of the new *Sutera* have been observed to have good garden performance and to tolerate wind, rain and to be suitable for USDA Hardiness Zones 9 to 11.

Pathogen & pest tolerance: To date, plants of the new *Sutera* have not been observed to be tolerant to pathogens and pests common to *Sutera* plants.

It is claimed:

1. A new and distinct *Sutera* plant named 'WINSUSNOGB' as illustrated and described.

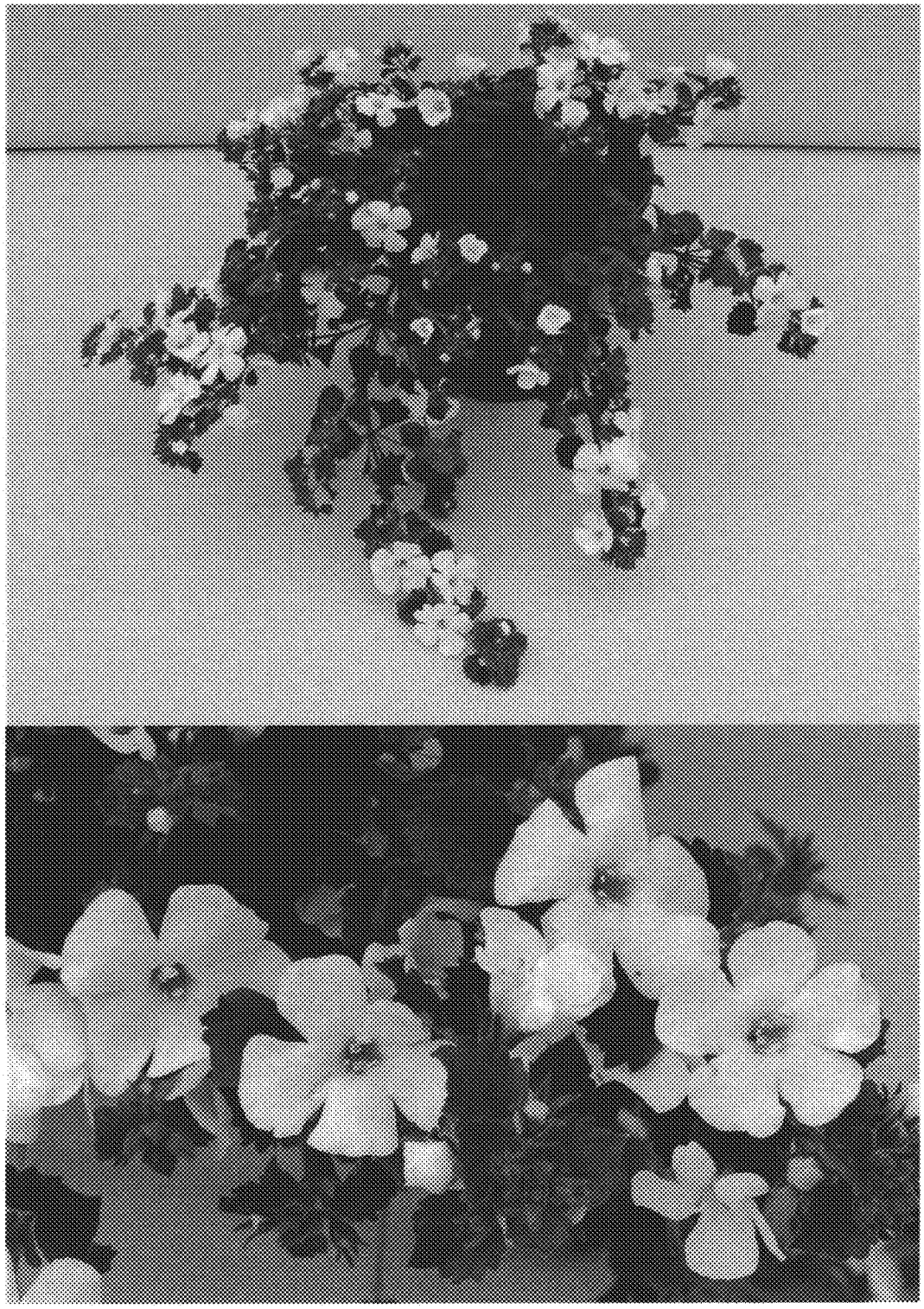

* * * * *